US00PP12756P2

(12) United States Plant Patent
Westhoff

(10) Patent No.: US PP12,756 P2
(45) Date of Patent: Jul. 2, 2002

(54) CALIBRACHOA PLANT NAMED 'WESCASUN'

(75) Inventor: Heinrich Westhoff, Sudlohn-Oeding (DE)

(73) Assignee: Josef & Heinrich Westhoff Gartenbau-Spezialkulturen, Südlohn-Oeding (DE)

( * ) Notice: Subject to any disclaimer, the term of this patent is extended or adjusted under 35 U.S.C. 154(b) by 1 days.

(21) Appl. No.: 09/797,249

(22) Filed: Mar. 1, 2001

(51) Int. Cl.[7] ..... A01H 5/00
(52) U.S. Cl. ..... Plt./263
(58) Field of Search ..... Plt./263, 356

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Calibrachoa plant named 'Wescasun', characterized by its semi-upright to cascading and uniform growth habit; freely branching habit; large flower size; numerous intense yellow-colored flowers; uniform flower coloration; and good weather tolerance.

1 Drawing Sheet

BACKGROUND OF THE INVENTION

The present Invention relates to a new and distinct cultivar of Calibrachoa plant, botanically known as *Calibrachoa hybrida*, and hereinafter referred to by the name 'Wescasun'.

The new Calibrachoa is a product of a planned breeding program conducted by the Inventor in Sudlohn-Oeding, Germany. The new Calibrachoa originated from a cross made by the Inventor of a proprietary selection of Calibrachoa identified as code number 98-107d, not patented, as the female, or seed, parent with a proprietary selection of Calibrachoa identified as code number 98-137-87, not patented, as the male, or pollen, parent. The new Calibrachoa was selected by the Inventor in 1999 on the basis of its large flower size. Plants of the new Calibrachoa differ from plants of the parent selections primarily in flower color and flower size.

Asexual reproduction of the new cultivar by terminal cuttings taken at Sudlohn-Oeding, Germany, has shown that the unique features of this new Calibrachoa are stable and reproduced true to type in successive generations.

SUMMARY OF THE INVENTION

Plants of the cultivar Wescasun have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Wescasun'. These characteristics in combination distinguish 'Wescasun' as a new and distinct cultivar:

1. Semi-upright to cascading and uniform growth habit.
2. Freely branching habit, dense and bushy.
3. Large flower size.
4. Numerous intense yellow-colored flowers.
5. Uniform flower coloration.
6. Good weather tolerance.

Plants of the cultivar Wescasun can be compared to plants of the Calibrachoa cultivar Million Bells Terracotta, not patented. However in side-by-side comparisons conducted by the Inventor in Sudlohn-Oeding, Germany, plants of the new Calibrachoa and the cultivar Million Bells Terracotta differ in the following characteristics:

1. Plants of the new Calibrachoa have larger flowers with larger sepals than plants of the cultivar Million Bells Terracotta.
2. Flower coloration of plants of the new Calibrachoa is more uniform than flower coloration of plants of the cultivar Million Bells Terracotta.
3. Plants of the new Calibrachoa have larger leaves than plants of the cultivar Million Bells Terracotta.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Calibrachoa. The photograph comprises a side perspective view of a typical plant of 'Wescasun'.

DETAILED BOTANICAL DESCRIPTION

In the following description, color references are made to The Royal Horticultural Society Colour Chart, 1995 edition, except where general terms of ordinary dictionary significance are used. Plants grown in containers were used for the following description. Plants were grown under conditions which closely approximate commercial production conditions during the spring in Sudlohn-Oeding, Germany. Plants used for the description were about 10 to 12 weeks from planting rooted cuttings.

Botanical classification: *Calibrachoa hybrida* cultivar Wescasun.

Parentage:

*Female parent.*—Proprietary selection of *Calibrachoa hybrida* identified as 98-107d, not patented.

*Male parent.*—Proprietary selection of *Calibrachoa hybrida* identified as 98-137-87, not patented.

Propagation:

*Type cutting.*—Terminal vegetative cuttings.

*Time to initiate roots.*—About two to three weeks at 20° C.

*Time to develop roots.*—About three to four weeks at 20° C.

*Root description.*—Numerous, fine, fibrous, and well-branched.

Plant description:

*Form.*—Annual flowering plant; initially upright then semi-upright to cascading; uniform, rounded appearance, plants eventually become spherical in overall shape. Freely branching with lateral branches forming at every node.

*Usage.*—Appropriate for hanging baskets, window boxes and patio containers.

*Plant height* (*from soil level to top of plant plane*).—About 21 to 23 cm.

*Plant length* (*from soil level to lateral branches apices*) .—About 50 to 67 cm.

*Plant diameter* (*area of spread*).—About 45 to 50 cm.

*Stem description.*—Main branches length: About 58 to 67 cm. Main branches, diameter: About 3.35 mm. Main branches, internode length: About 1.8 cm. Lateral branches, length: About 21 to 23 cm. Lateral branches, diameter: About 2 mm. Lateral branches, internode length: About 1.8 cm. Texture: Dense white pubescence. Strength: Strong, wiry. Color: 146C.

*Foliage description.*—Leaves simple, generally symmetrical and long persisting; sessile. Arrangement: Alternate. Length: About 3.7 to 4.1 cm. Width: About 1.3 to 1.6 cm. Shape: Oblanceolate to elliptic. Apex: Obtuse. Base: Attenuate. Margin: Entire. Aspect: Mostly flat. Texture: Dense white pubescence. Color: Young foliage, upper surface: 146B. Young foliage, lower surface: 146C. Mature foliage, upper surface: 147A; veins, 146D. Mature foliage, lower surface: 147B, veins, 146D.

Flower description:

*Flower type and habit.*—Large-sized flowers; flowers face upright or outward; single, axillary. Flowers not persistent. Freely flowering with flowers forming at every axil.

*Natural flowering season.*—Spring until frost in the autumn; flowering continuous.

*Flower longevity on the plant.*—About one week.

*Flower size.*—Diameter: About 3.2 to 3.5 cm. Depth (height): About 2.1 to 2.4 cm. Tube length: About 1.8 cm. Throat diameter, distal end: About 9 mm. Tube diameter, proximal end: About 2.5 mm.

*Flower buds* (*just showing color*).—Length: About 2.5 cm. Diameter: About 5 mm. Shape: Oblong. Color: Towards apex, 14A to 14C, main vein, 166A, and lateral veins, 166B to 173A; towards base, 14D, veins, 166A.

*Corolla.*—Arrangement/appearance: Single whorl of five petals, fused into flared trumpet. Petal length from throat: About 1.4 cm. Petal width: About 1.6 cm. Petal shape: Roughly spatulate with obtuse apex. Petal margin: Entire. Petal texture: Smooth, satiny. Color: Petal, upper surface, when opening: 14A; random spots, 169A. Petal, lower surface, when opening: 14D; main vein, 166A; random spots, 186A. Petal, upper surface, opened flower: 14B to 14C; random spots, 169C to 169D; main vein, 177A; lateral veins, 177A to 177B; fading to 16A with random spots, 182A. Petal, lower surface, opened flower: 14D; random spots, 186B; main vein, 166A; lateral veins, 182B. Flower throat (in side): 17A to 17B; veins, 166A to 166C. Flower tube (outside): 14C; veins, 166A to 166C.

*Sepals.*—Arrangement/appearance: Single whorl of five sepals, star-shaped. Length: About 2 cm. Width: About 4 mm. Shape: Lanceolate. Apex: Acute. Margin: Entire. Texture: White pubescence. Color: Upper surface: 147A. Lower surface: 147B.

*Peduncles.*—Length: About 2.3 cm. Width: About 1 mm. Strength: Flexible and wiry, flowers held upright or outward. Color: Upper surface: 147A. Lower surface: 146B.

*Reproductive organs.*—Stamens: Quantity per flower: 5. Filament color: 144B. Anther shape: Four-parted, oval. Anther length: About 1.1 mm. Anther color: 15D. Pollen amount: Moderate. Pollen color: 15D. Pistils: Quantity per flower: 1. Pistil length: About 1.5 cm. Stigma shape: Oval. Stigma color: Immature: 144B. Mature: 144A. Style length: About 1 cm. Style color: 144C. Ovary color: 144B to 144C.

*Seed.*—Seed production has not been observed.

Disease resistance: Plants of the new Calibrachoa have not been noted to be resistant to pathogens common to Calibrachoa.

Weather tolerance:

Plants of the new Calibrachoa are tolerant to rain and wind.

It is claimed:

1. A new and distinct cultivar of Calibrachoa plant named 'Wescasun', as illustrated and described.

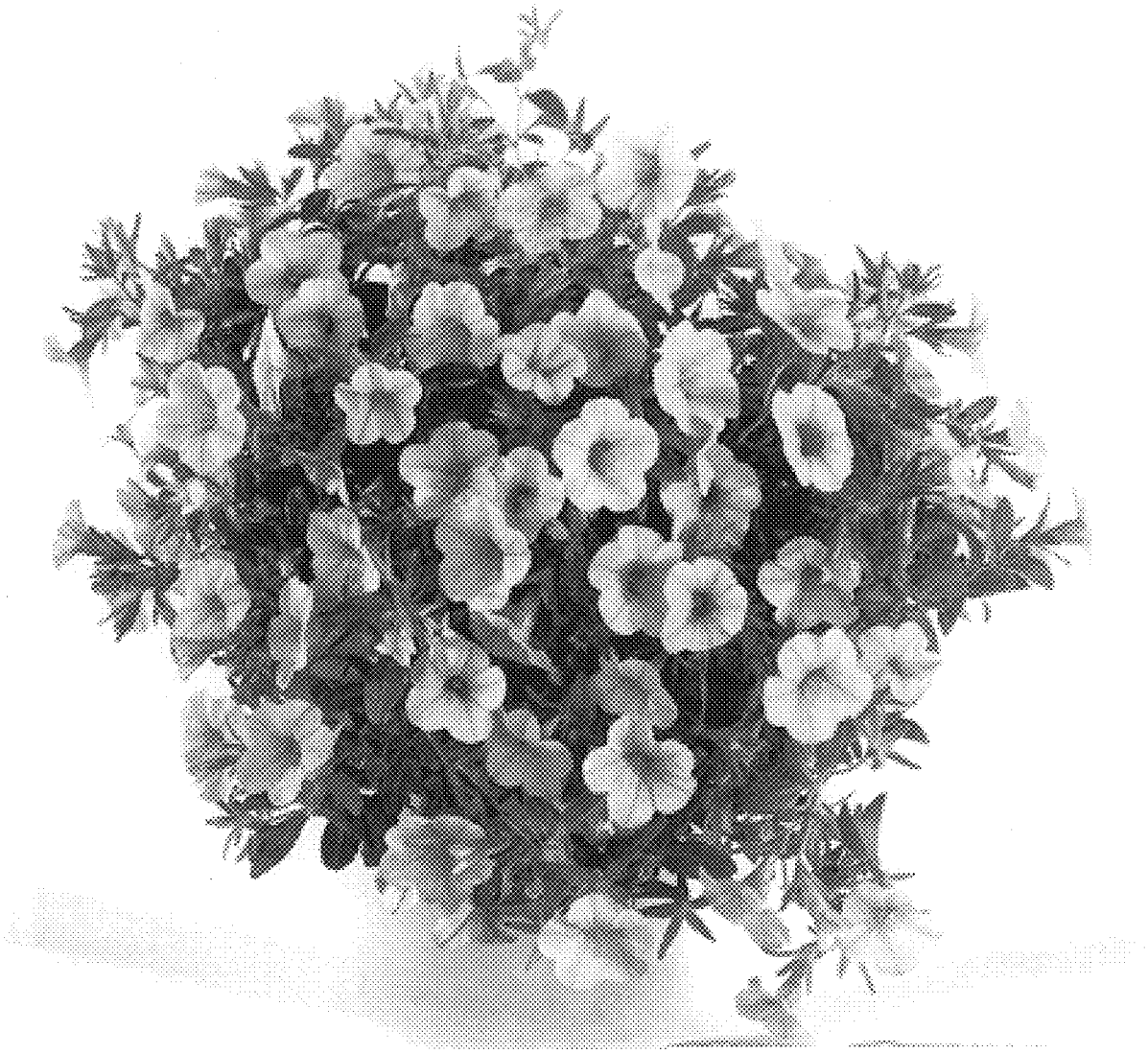

* * * * *